(12) United States Patent
Nakamura et al.

(10) Patent No.: US 10,537,257 B2
(45) Date of Patent: Jan. 21, 2020

(54) BIOLOGICAL INFORMATION READING DEVICE

(71) Applicants: SHINANO KENSHI CO., LTD., Nagano (JP); CHUO UNIVERSITY, Tokyo (JP)

(72) Inventors: Hiroyuki Nakamura, Nagano (JP); Tetsuji Dohi, Tokyo (JP); Kota Kudo, Tokyo (JP)

(73) Assignees: SHINANO KENSHI CO., LTD., Tokyo (JP); CHUO UNIVERSITY, Tokyo (JP)

( * ) Notice: Subject to any disclaimer, the term of this patent is extended or adjusted under 35 U.S.C. 154(b) by 204 days.

(21) Appl. No.: 15/567,881

(22) PCT Filed: Apr. 19, 2016

(86) PCT No.: PCT/JP2016/062405
§ 371 (c)(1),
(2) Date: Oct. 19, 2017

(87) PCT Pub. No.: WO2016/171140
PCT Pub. Date: Oct. 27, 2016

(65) Prior Publication Data
US 2018/0153423 A1   Jun. 7, 2018

(30) Foreign Application Priority Data

Apr. 21, 2015  (JP) .................................. 2015-087155
Apr. 19, 2016  (JP) .................................. 2016-083812

(51) Int. Cl.
*A61B 5/024*   (2006.01)
*A61B 5/0255*  (2006.01)
(Continued)

(52) U.S. Cl.
CPC ........ *A61B 5/02444* (2013.01); *A61B 5/0255* (2013.01); *A61B 5/11* (2013.01);
(Continued)

(58) Field of Classification Search
CPC . A61B 5/02444; A61B 5/0255; A61B 5/7207; A61B 2562/0247; A61B 2562/028; A61B 5/742
See application file for complete search history.

(56) References Cited

U.S. PATENT DOCUMENTS 6,293,915 B1   9/2001  Amano et al.
7,217,244 B2   5/2007  Suzuki et al.
(Continued)

FOREIGN PATENT DOCUMENTS

JP   2000051164 A   2/2000
JP   2004-208711 A  7/2004
(Continued)

OTHER PUBLICATIONS

This above reference was cited in JP Office Action to JP Application No. 2016-083812 dated Jul. 2, 2019, which is enclosed with an English translation.

*Primary Examiner* — Eric F Winakur
(74) *Attorney, Agent, or Firm* — Cowan, Liebowitz & Latman, P.C.; Mark Montague

(57) ABSTRACT

While there are various methods for acquiring biological information based on pulse waveforms, none of the methods have been implemented in a biological information reading device that can be constantly operated stably. Provided is a biological information reading device which has achieved high accuracy by removing disturbance components from a pulse signal acquired by means of a multi-axis pressure sensor or a plurality of single-axis pressure sensors, and which can be attached to an examinee at all times for continuous observation taking advantage of the small and light-weight feature of the pressure sensors.

5 Claims, 8 Drawing Sheets

(51) Int. Cl.
  *A61B 5/00* (2006.01)
  *A61B 5/11* (2006.01)
  *G01L 9/12* (2006.01)

(52) U.S. Cl.
  CPC ............ *A61B 5/681* (2013.01); *A61B 5/6843* (2013.01); *A61B 5/721* (2013.01); *A61B 5/7207* (2013.01); *A61B 5/6824* (2013.01); *A61B 5/742* (2013.01); *A61B 2562/028* (2013.01); *A61B 2562/0247* (2013.01); *G01L 9/12* (2013.01)

(56) References Cited

U.S. PATENT DOCUMENTS

| | | | |
|---|---|---|---|
| 9,005,141 B1* | 4/2015 | Najafi | A61B 5/7264 600/595 |
| 2005/0038347 A1 | 2/2005 | Suzuki et al. | |
| 2009/0322540 A1* | 12/2009 | Richardson | A61B 5/0002 340/573.7 |
| 2011/0077537 A1 | 3/2011 | Ebara et al. | |
| 2014/0330134 A1* | 11/2014 | Chon | A61B 5/7282 600/508 |
| 2015/0374296 A1* | 12/2015 | Baru | A61B 5/0205 600/377 |

FOREIGN PATENT DOCUMENTS

| | | |
|---|---|---|
| JP | 2004-313468 A | 11/2004 |
| JP | 2005-253865 A | 9/2005 |
| JP | 2006-192288 A | 7/2006 |
| JP | 2007-007075 A | 1/2007 |
| JP | 2010-194108 A | 9/2010 |
| JP | 2011-072645 A | 4/2011 |
| JP | 2011-182968 A | 9/2011 |
| JP | 2011-239840 A | 12/2011 |
| WO | 99/26529 A1 | 6/1999 |

* cited by examiner

BIOLOGICAL INFORMATION READING DEVICE

CROSS REFERENCE TO RELATED APPLICATIONS

This is a U.S. national stage of application No. PCT/JP2016/062405, filed on Apr. 19, 2016. Priority under 35 U.S.C. § 119(a) and 35 U.S.C. § 365(b) is claimed from Japanese Patent Application Nos. 2015-087155, filed on Apr. 21, 2015 and 2016-083812, filed on Apr. 19, 2016, the disclosures of which are also incorporated herein by reference.

TECHNICAL FIELD

The present invention relates to a biological information reading device for reading a pulse wave as a biological signal by a pressure sensor. In particular, the present invention relates to a biological information reading device for measuring a blood pressure on the basis of a pulse waveform.

BACKGROUND ART

An oscillometric method and a tonometry method have been conventionally known as a blood pressure measurement method. The oscillometric method is to measure blood pressure by, in a process of putting a cuff on an upper arm or wrist to compress a blood vessel and to make a blood flow therein once stop and then loosing the cuff to gradually reduce the pressure, and checking a cuff pressure which reflects pulsation of a blood vessel wall synchronizing with cardiac pulsation. Blood pressure measurement by the oscillometric method using a cuff is non-invasive, and has been automatically performed in a mechanical manner, for easy blood pressure measurement. However, the blood pressure measurement device is too large to carry around, takes several ten seconds to one minute to perform measurement, and requires resting during blood pressure measurement, and thus, the frequency of blood pressure measurement disadvantageously interferes with daily life.

The tonometry method is a method for obtaining a blood pressure value while pressing a sensor having a flat contact pressure against an artery, and measuring variation in inner pressure in the artery pulsating against the sensor. A conceptual diagram of blood pressure measurement by the tonometry method is illustrated in FIG. 11. FIG. 11 is a schematic cross-sectional view of a portion of and around a human hand, where a radial artery is positioned on a radius bone, and a sensor array is put on a skin immediately above the radial artery. The sensor array generally has a flat shape, so that upon pressing the sensor array against the skin, the skin facing a sensor contact surface is also expanded flat.

In the sensor array, a plurality of sensors are arranged in an array as the name suggests, and a sensor positioned around a portion immediately above the radial artery can capture an arterial pulse wave in the largest dynamic range. Therefore, if a sensor array has a size not less than a certain size, it may be put on a roughly estimated position of a blood vessel to adopt a signal of the largest dynamic range among signals obtained from respective sensors.

CITATION LIST

Patent Literature

{PTL1}: JP 2011-239840 A
{PTL2}: JP 2005-253865 A
{PTL3}: JP 2007-007075 A

SUMMARY OF INVENTION

Technical Problem

PTL 1 (JP 2011-239840 A) discloses a technique for correcting a pressing direction of a sensor in an existing tonometry method, using a triaxial pressure sensor. However, improvement of degree of freedom in applying a measurement device or degree of stability in measurement is not suggested, and continuously stable environment of blood pressure measurement is not provided.

Furthermore, PTL 2 (JP 2005-253865 A) discloses a technique for detecting body movement, by providing an acceleration sensor different from a biological information acquisition sensor. However, even when body movement can be detected, if a pulse waveform during body movement is treated only as invalid, it cannot be used in a condition of continuous body movement (such as sports), and cannot satisfy a requirement for continuous blood pressure measurement.

Furthermore, as a different example, PTL 3 (JP 2007-007075 A) discloses a technique for calculating a blood pressure value on the basis of a pulse wave. However, calculation is performed on condition that a pulse wave is stably acquired without consideration that a person has difficulty in acquiring pulse waves in daily life, and this technique also does not satisfy the requirement for continuous blood pressure measurement.

As described above, in the related art, it cannot accurately find variation in blood pressure which is an important prediction factor for disease, and occurs for a short time or suddenly owing to an ambient environment or physical or psychological condition. Therefore, it is required a highly accurate measurement method from which the above described disturbances can be removed regardless of body movement.

An object of the present invention is to provide a biological information reading device put on a human body to always continuously acquire pulse wave signals as biological information, and enabling highly accurate measurement by removing influence of disturbances caused by body movement or the like as much as possible.

Solution to Problem

According to a first aspect of the present invention, a biological information reading device for reading biological information comprises a biological signal acquisition unit for acquiring a biological signal from a living body as an electric signal; a disturbance removal unit for removing a disturbance component in the electric signal acquired by the biological signal acquisition unit; and a biological information calculation unit for calculating biological information on the basis of the electric signal from which disturbance is removed by the disturbance removal unit, the biological signal acquisition unit including a multiaxial pressure sensor, pressure detection axes thereof having different directional components respectively.

According to another aspect of the present invention, a biological information reading device for reading biological information comprises a biological signal acquisition unit for acquiring a biological signal from a living body as an electric signal; a disturbance removal unit for removing a disturbance component in an electric signal acquired by the biological signal acquisition unit; and a biological information calculation unit for calculating biological information on the basis of the electric signal from which disturbance is removed by the disturbance removal unit, the biological signal acquisition unit including a plurality of uniaxial pressure sensors.

Furthermore, according to another aspect of the present invention, a biological information reading device for reading biological information comprises a biological signal acquisition unit for acquiring a biological signal from a living body as an electric signal; a disturbance removal unit for removing a disturbance component in an electric signal acquired by the biological signal acquisition unit; and a biological information calculation unit for calculating biological information on the basis of the electric signal from which disturbance is removed by the disturbance removal unit, the biological signal acquisition unit including a multiaxial pressure sensor and an uniaxial pressure sensor pressure, detection axes of the multiaxial pressure sensor having different directional components respectively.

The disturbance removal unit can remove one or both of an influence caused by displacement of the multiaxial pressure sensor or the uniaxial pressure sensor from a position immediately above a blood vessel, and an influence caused by body movement being movement of a living body.

The biological information calculation unit may include a pulse wave circulatory dynamics calculation unit for calculating biological information by adopting at least one of mutual time intervals starting from one of characteristic points including a starting point, a percussion wave, a tidal wave and a dicrotic wave to another, and time intervals of the characteristic points in adjacent pulse wave signals as a circulatory dynamics value of a pulse wave, The pulse wave circulatory dynamics calculation unit may include a velocity pulse wave calculation unit for deriving a first differentiation of a stable pulse wave signal to acquire starting point, percussion wave, tidal wave, and dicrotic wave information from zero crossing points in the velocity pulse wave.

The multiaxial pressure sensor or the uniaxial pressure sensor may be a MEMS sensor, or a capacitive sensor.

Advantageous Effects of Invention

According to the present invention, continuous highly accurate measurement of pulse wave signals can be achieved, and thus, biological information can be always continuously acquired.

DESCRIPTION OF EMBODIMENTS

Hereinafter, embodiments of the present invention will be described with reference to the drawings.

Before detailed description, common matters in the present description will be described.

In the present invention, "pulse wave" represents a wave of pulsation detected on the basis of the pressure of a blood vessel, and "stable pulse wave" represents a pulse wave from which influences of displacement of a sensor and body movement are removed.

Figure 1:
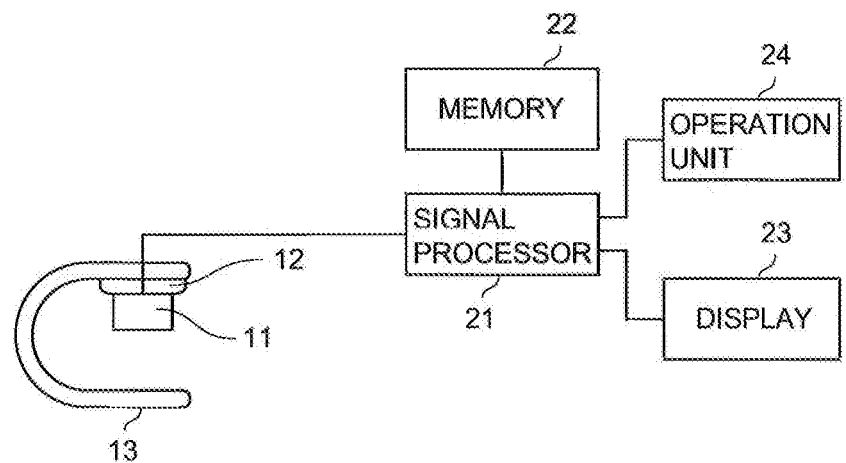
FIG. 1 is a block diagram showing a configuration of a pulse waveform acquisition device according to an embodiment of the present invention.
Figure 2:
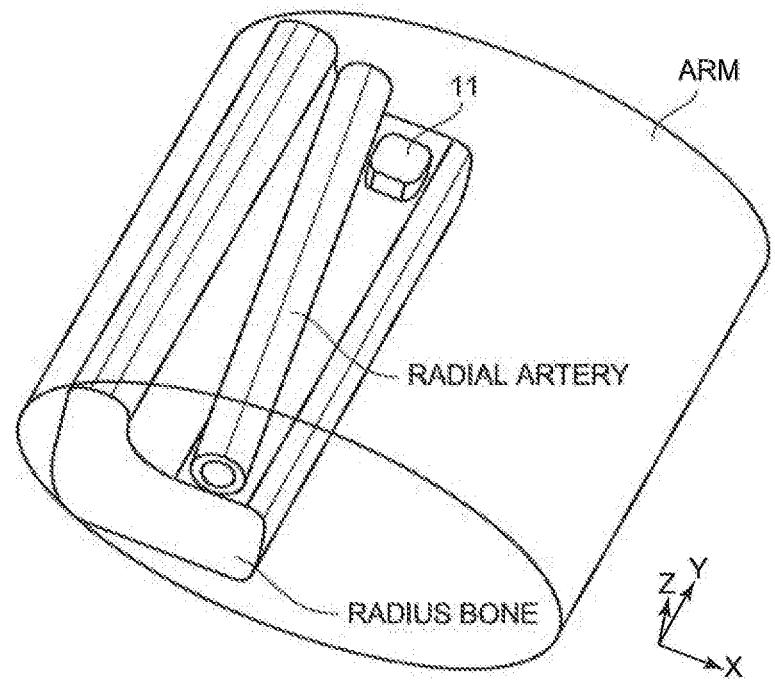
FIG. 2 is a conceptual diagram showing a first embodiment of the present invention.

FIG. 1 shows a configuration of a pulse wave acquisition device for reading a pulse wave as biological information according to a first embodiment of the present invention. As shown in FIG. 1, the pulse wave acquisition device includes, as a sensor of a detection unit for acquiring a pulse wave of a human body, an orthogonal triaxial pressure sensor 11 for detecting a pressure in three orthogonal X, Y, and Z axes. The orthogonal triaxial pressure sensor (hereinafter, referred to as triaxial pressure sensor) is attached to an affixing unit 13 through an elastic member 12. The affixing unit 13 is used to closely press the triaxial pressure sensor 11 against the skin of a wrist of a human body to be measured in the vicinity of a radial artery. FIG. 2 shows the triaxial pressure sensor 11 attached to the affixing unit 13. The affixing unit 13 has a curved resin structure to bring the triaxial pressure sensor 11 into contact with the skin of the wrist of the human body, and has a flat inner surface portion to which the triaxial pressure sensor 11 is attached, and the triaxial pressure sensor can be fixed to the wrist. The triaxial pressure sensor 11 is attached to the affixing unit 13 through the elastic member 12 so that the triaxial pressure sensor 11 is pressed against the skin with a moderate pressure.

The affixing unit 13 has a band, as a conventional one, which opens at one side to be put on the wrist for fixing the affixing unit 13 put on the wrist to fixedly press the triaxial pressure sensor 11 to the skin of the wrist. This structure for fixing to the wrist is the same in function as that of a conventional cuff which is put on a wrist to acquire a pulse wave. Furthermore, the affixing unit 13 may be made of a soft material, such as a cloth, similar to that of the cuff, as long as the affixing unit 13 has a structure bringing the triaxial pressure sensor 11 into contact with the skin with a moderate pressure.

FIG. 1 shows a block diagram illustrating the pulse wave acquisition device according to the present embodiment. The pulse wave acquisition device according to the present embodiment includes a signal processor 21 receiving input of detection output from the triaxial pressure sensor 11 attached to the affixing unit 13, and removing disturbance from a detected triaxial pressure information to calculate a pulse waveform or a blood pressure, a memory 22 storing information such as a parameter or calculation formula used for calculation of a blood pressure in the signal processor 21, waveform data as a result of calculation, data from the triaxial pressure sensor 11, and the like, a display 23 displaying an acquired pulse waveform or blood pressure information estimated and calculated on the basis of a pulse wave, or operation information such as operation instruction, and an operation unit 24 receiving input of operation information such as start or end of detection.

The triaxial pressure sensor corresponds to a biological signal acquisition unit defined in the claims, the signal processor 21 and the memory 22 respectively correspond to a disturbance removal unit and a biological information calculation unit calculating biological information, defined in the claims, and the pulse wave reading device correspond to a biological information reading device.

Here, the display 23 and the operation unit 24 may be integrally formed. For example, operation input employs touch panel input method, display and operation input may be integrated.

The signal processor 21, the memory 22, the display 23, and the operation unit 24 may be accommodated in a chassis separated from the affixing unit 13, but may be provided in the affixing unit 13 if they are reduced in size. Furthermore, a power supply is provided, but not illustrated in the drawings, in the chassis for energizing the pulse wave acquisition device. The power supply may be a battery or one using commercial power.

This pulse wave acquisition device comprises an unillustrated external interface through which output of the signal processor 21 can be supplied to an external device. The external interface may be used for taking the pulse wave acquisition device as a monitor for a patient, or for collecting pulse waveforms, such as acquiring pulse waveforms during exercise, by an external device.

FIG. 2 is an explanatory diagram illustrating the principle of measurement of a pulse wave acquired by the pulse wave acquisition device according to the present embodiment. The triaxial pressure sensor 11 is put on a skin surface in the vicinity of a radial artery of a wrist to detect a pressure in three X, Y, and Z axes. A Z axis direction indicates an upward direction from the skin surface of the wrist, that is, a direction in which an arterial blood pressure is applied toward the skin, an X axis direction indicates a transverse direction of the wrist, and a Y axis direction indicates a longitudinal direction of the wrist.

Removal of disturbance will be described with reference to FIGS. 3 and 4.

As described above, one triaxial pressure sensor is used as the sensor, and body movement disturbing an acquired pulse waveform is assumed as the disturbance.

Figure 3B:
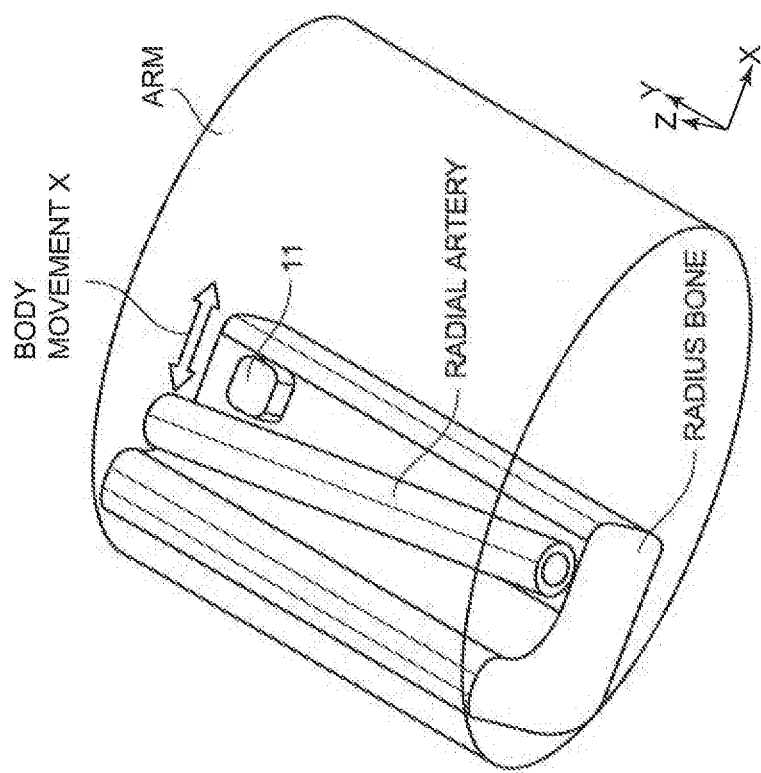
FIG. 3 shows an arrangement of a sensor according to the first embodiment of the present invention.
Figure 3A:
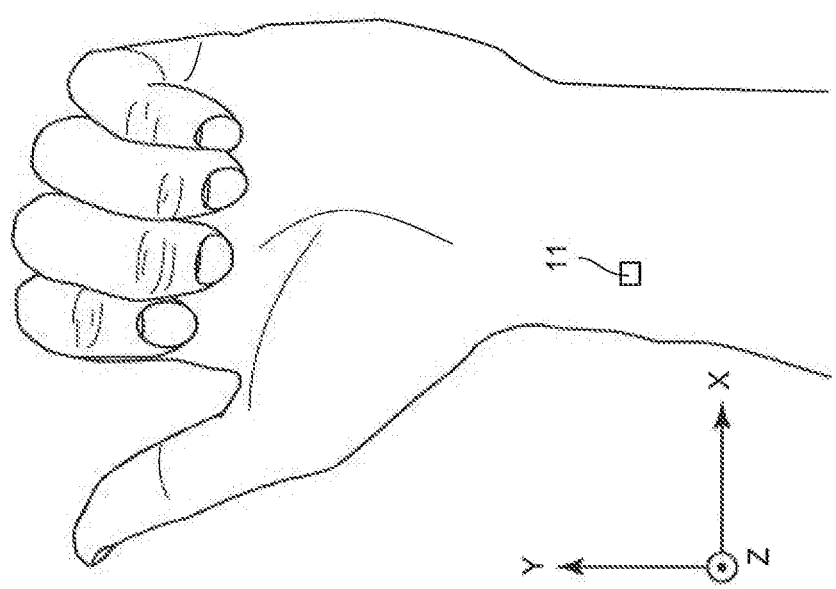

As shown in FIG. 3, the triaxial pressure sensor 11 is arranged immediately above the radial artery. In this condition, it is assumed that body movement occurs in the X axis direction. As pulse waveform signals from the triaxial pressure sensor 11, attention is focused on a Z-axis sensor signal and an X-axis sensor signal. The Z-axis sensor signal is suitable for acquisition of a pulse waveform, and the X-axis sensor signal is suitable for acquisition of a body movement component in the X direction.

Figure 4:
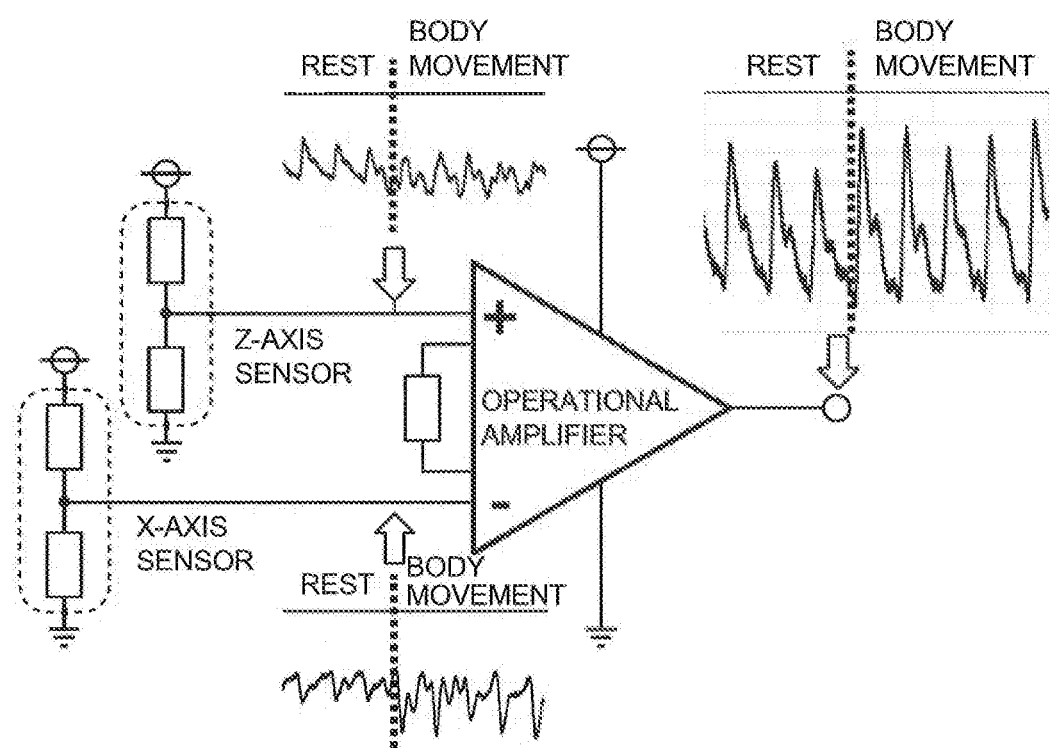
FIG. 4 shows a concept of signal processing according to the first embodiment of the present invention.

Therefore, as shown in FIG. 4, output from a Z-axis sensor and output from an X-axis sensor, of output signals from the triaxial pressure sensor, is input to an operational amplifier 211 to remove a body movement component generated in the X axis direction. Thus, as shown in FIG. 4, the body movement component may be removed from an output signal from the operational amplifier 211.

A pulse wave is to be generated by the increase or decrease in blood flow, so that, when viewed in cross-section of a blood vessel, the blood vessel becomes an extending and contracting manner in a radial direction, and a substantially isotropic pressure wave is generated outward from the center of the blood vessel. Therefore, on a skin nearest to a blood vessel, a pulse wave is strongly captured as the pressure wave in a Z-axis component of the triaxial pressure sensor, but the X-axis sensor and the Y-axis sensor also include pulse wave components, although the absolute values thereof are relatively small.

Note that in the above description, description of the Y-axis is omitted for simple description, but consideration of a signal from the Y-axis sensor will provide further better removal of the disturbance.

Furthermore, in the description with reference to FIG. 4, removal of the component of the X-axis sensor signal from the Z-axis sensor signal, which is achieved by the operational amplifier of an analog circuit, has been described as an example, but signal processing, such as removal of disturbance in the signal processor 21, or calculation of a blood pressure value on the basis of a pulse waveform, may be achieved as a matter of course by a digital calculation circuit.

Note that, as described above, since the pulse wave components are also superimposed on the X-axis and Y-axis sensors other than the Z-axis sensor, these sensor signals of the axes may be combined or may be subjected to hardware/software calculation to obtain the stable pulse wave, even when the triaxial pressure sensor is not positioned immediately above the blood vessel, and the degree of freedom in arrangement which is similar to that in a sensor array method can be provided. Furthermore, an appropriate arrangement position of the triaxial pressure sensor is understood on the basis of the waveforms of the X-axis and Y-axis sensors, so that an appropriate position can be searched while viewing the waveforms of the X-axis and Y-axis sensors.

For searching the appropriate position of the sensor, a guiding method using the change in sound volume or sound wave length, or light intensity or light wave length is preferably employed.

Specifically, a sensor using a micro electro-mechanical systems (MEMS) called as micromachine, a capacitive sensor, or the like can be applied as the triaxial pressure sensor.

In the present embodiment, the circuit using the operational amplifier having excellent performance in amplification of a weak output signal, such as sensor output, and removal of common mode noise has been described as an example, but an amplifier circuit using an inverting or non-inverting amplifier circuit or a transistor, or further having a filter circuit may be employed.

In the first embodiment, use of a single triaxial pressure sensor has been described, but another method will be described with reference to FIGS. 5 to 8.

Figure 5B:
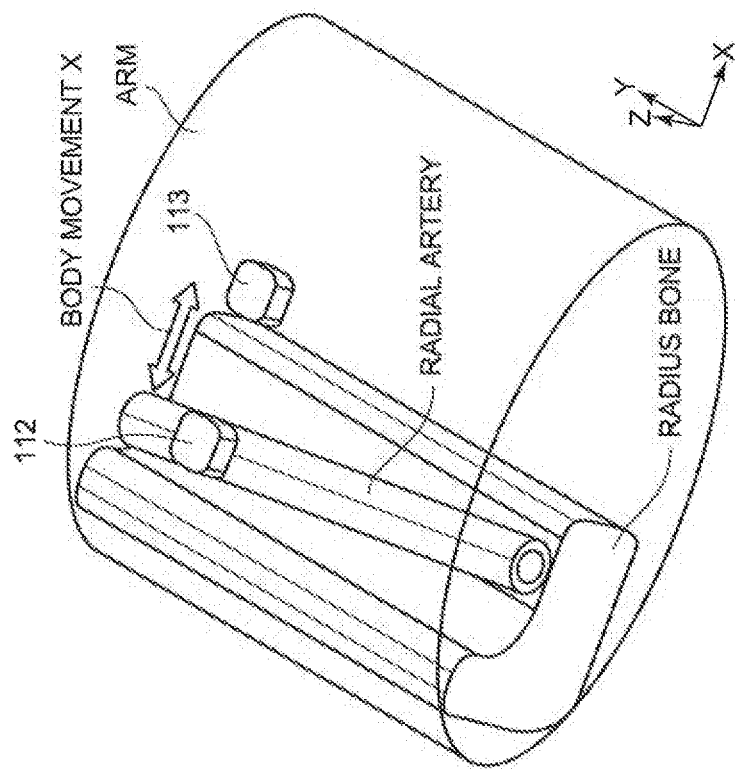
FIG. 5 shows an arrangement of sensors according to a second embodiment of the present invention.
Figure 5A:
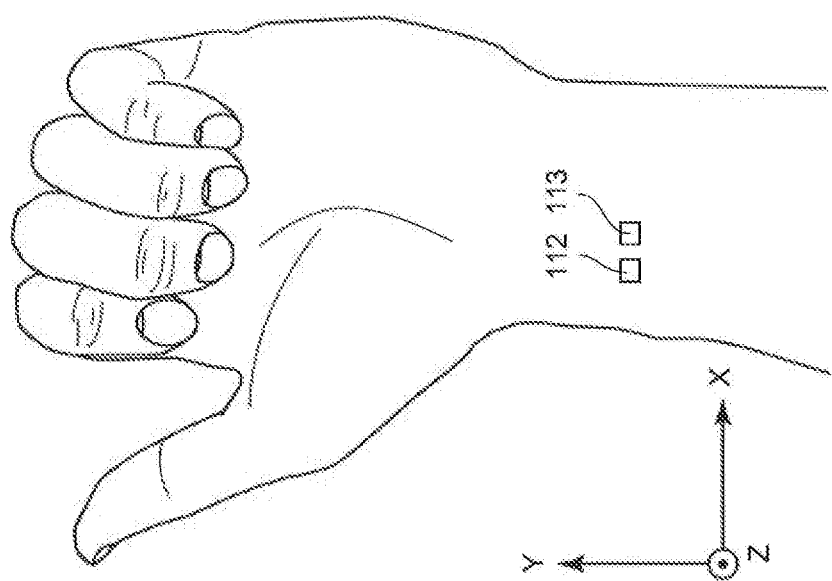

The configuration shown in FIG. 5 as a second embodiment is substantially same with that shown in FIG. 3, but, in the second embodiment, two triaxial pressure sensors are used as sensors. One of the two triaxial pressure sensors is arranged immediately above a radial artery, as a pulse wave detection sensor, and the other is arranged in the vicinity of the blood vessel, as an inertia detection sensor for body movement.

Figure 6:
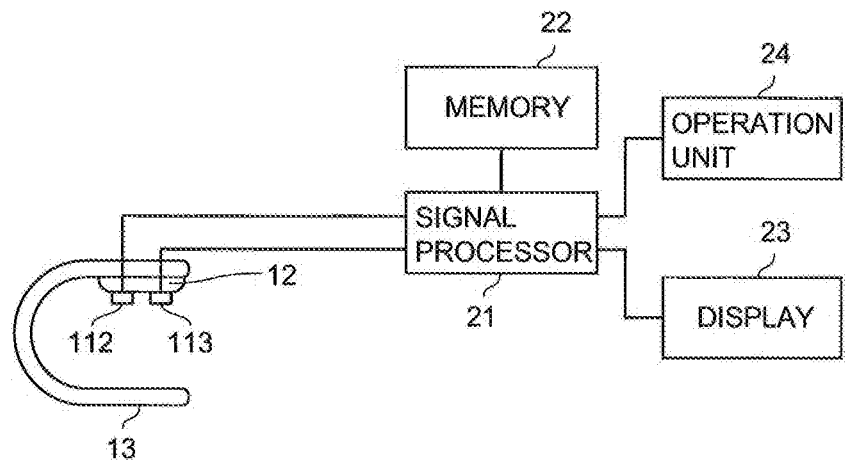
FIG. 6 is a block diagram showing a configuration of a pulse waveform acquisition device according to the second embodiment of the present invention.

FIG. 6 is a block diagram showing a configuration of a pulse waveform reading device according to the second embodiment, where two sensors are used. As the sensors, the pulse wave detection sensor 112 and the inertia detection sensor 113 for body movement detection which detects body movement are used. The other configuration is the same as that in the first embodiment, and description thereof will be omitted.

Figure 7:
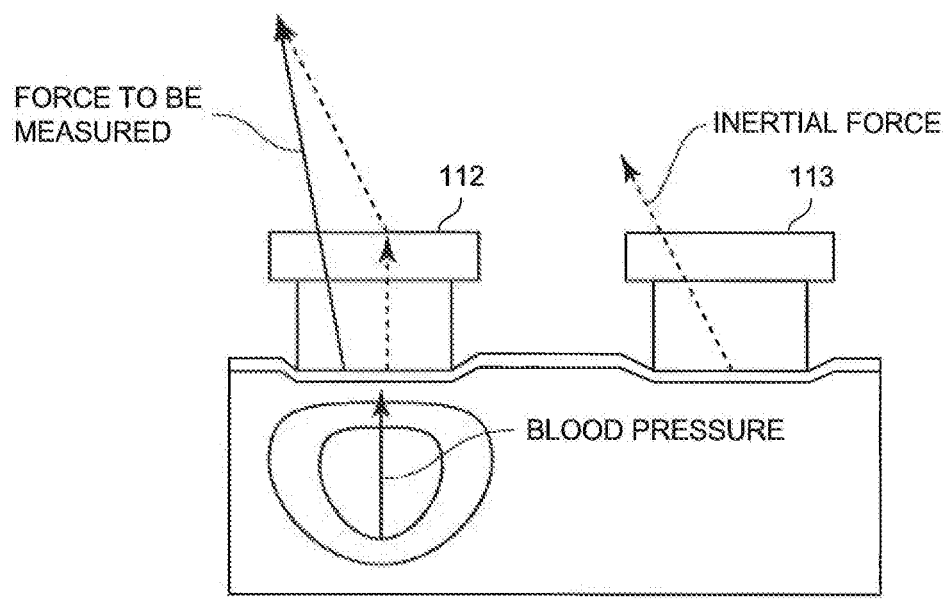
FIG. 7 shows forces influenced by body movement and detected by a sensor, according to the second embodiment of the present invention.

FIG. 7 shows vector expression of forces acting on the pulse wave detection sensor 112 and the inertia detection sensor 113. The pulse wave detection sensor 112 detects a force obtained by combining a blood pressure in the radial artery and an inertial force acting on the pulse wave detection sensor 112 by body movement. The inertia detection sensor 113 is not affected by the blood pressure in the radial artery, and detects only the inertial force. Therefore, as expressed by the following formula, when an output detected by the inertia detection sensor 113 is subtracted from an output from the pulse wave detection sensor 112, a disturbance (noise) caused by an inertial force generated by a body movement added to a pulse waveform output from the pulse wave detection sensor 112 can be removed.

[Blood pressure pulse wave]=[Pulse wave detection sensor (Blood pressure pulse wave+Inertial force)]−[Inertia detection sensor (Inertial force)]

Figure 8:
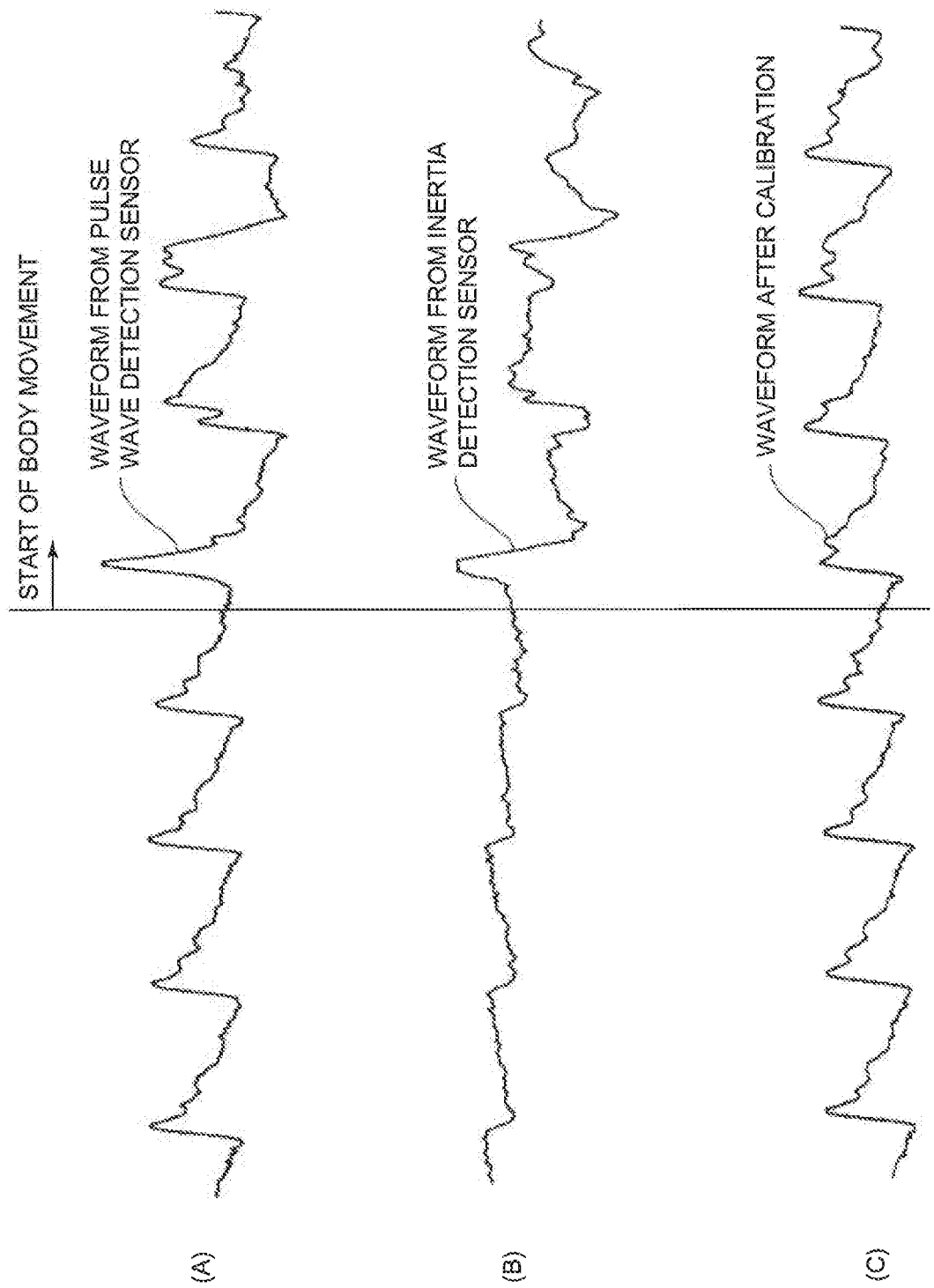
FIG. 8 shows signal processing according to the second embodiment of the present invention. A waveform (a) represents an output waveform from a pulse wave detection sensor, a waveform (b) represents an output waveform from an inertia detection sensor, and a waveform (c) represents an output waveform after calibration.

FIG. 8 shows a Z-axis component waveform of the pulse wave detection sensor 112, a Z-axis component waveform of the inertia detection sensor 113, and a waveform having a calibrated inertial force, where a wrist is moved in the X axis direction (horizontally right and left) as the body movement. A waveform (a) shown in FIG. 8 represents an output waveform from the pulse wave detection sensor 112, a waveform (b) shown in FIG. 8 represents an output waveform from the inertia detection sensor 113, and a waveform (c) shown in FIG. 8 represents a waveform after calibration.

As described above, the inertia detection sensor is arranged in the vicinity of the pulse wave detection sensor to perform subtraction of an output from the inertia detection sensor, from an output from the pulse wave detection sensor, and variation in pulse waveform can be reduced, which is caused by an inertial force generated by body movement and acting on the sensor.

In the second embodiment described above, a pressure is applied on the Z axis direction as in the example of the first embodiment.

The pulse wave detection sensor 112 is arranged immediately above the blood vessel, and the inertia detection sensor 113 is arranged at a position different from that of the pulse wave detection sensor 112, but a relative positional relationship between the inertia detection sensor 113 and the pulse wave detection sensor 112 is not directly defined. Specifically, the two sensors are not fixed in their mutual positions by means of a fixing device or the like, but, for example, attached by means of adhesive tapes or the likes individually. That is to say, the sensors are handled such that elasticity of the skin is maintained.

Furthermore, a triaxial pressure sensor may be used as the above pulse wave detection sensor 112 and inertia detection sensor 113 such that only a pressure in the Z axis direction is used to acquire a pulse waveform and remove body movement. Furthermore, two triaxial pressure sensor are preferably used such that axis components of the sensors are used to remove body movements for each axis.

Furthermore, an uniaxial pressure sensor can be used as the inertia detection sensor 113 such that three axis components of the pulse wave detection sensor 112, and a single axis component of the inertia detection sensor 113 are used to acquire a pulse waveform and remove a body movement component.

In this configuration, the inertia detection sensor 113 may be designed to have a detection direction for a specific use condition such that the body movement component is preferably removed. For example, in hitting a ball with a tennis racket, since body movement of an arm is in the Z axis direction, the detection direction of the uniaxial pressure sensor is preferably positioned parallel to the Z-axis. In running, since body movement of an arm is in the X axis direction, the detection direction of the uniaxial pressure sensor is preferably positioned parallel to the X-axis. In jabbing in boxing, since the body movement of an arm is in the Y-axis direction, the detection direction of the uniaxial pressure sensor is preferably positioned parallel to the Y-axis.

Furthermore, the detection direction of the uniaxial pressure sensor does not need to be parallel to any of the X, Y, and Z-axes, and may be configured to be appropriately set according to a use condition.

Furthermore, as in the first embodiment, an operational amplifier of an analog circuit may be used for waveform processing to take in outputs from the pulse wave detection sensor 112 and the inertia detection sensor 113 to this operational amplifier, and subtract a detected waveform from the inertia detection sensor, from a detected waveform from the pulse wave detection sensor, so that influence of disturbance caused by body movement can be reduced.

Note that a relative positional relationship between the pulse wave detection sensor 112 and the inertia detection sensor 113 is mainly defined by a skin condition. In the sensor array method, a portion where sensors are positioned is pressed against a skin surface with a constant pressure, so that elasticity of the skin is lost, and a pressure wave immediately above the blood vessel, which is derived from a pulse wave, is also damped. Therefore, in the sensor array method, the pressing force needs to be strictly managed so as to be maintained constant, but when body movement is in the Z axis direction, the sensor cannot be pressed with a constant pressure, and a pulse waveform cannot be obtained during that time. In particular, in the sensor array method, the sensors have a larger mass than that of a normal pressure sensor, vibration is excessively increased with body movement, and thus, stable acquisition of a pulse wave is made difficult.

In contrast, in the method according to the present invention, a plurality of (two or more) pressure sensors of light and small can be used to effectively remove a body movement signal.

Although removal of body movement as the disturbance has been described, significant influence of the body movement will be described again.

Figure 9:
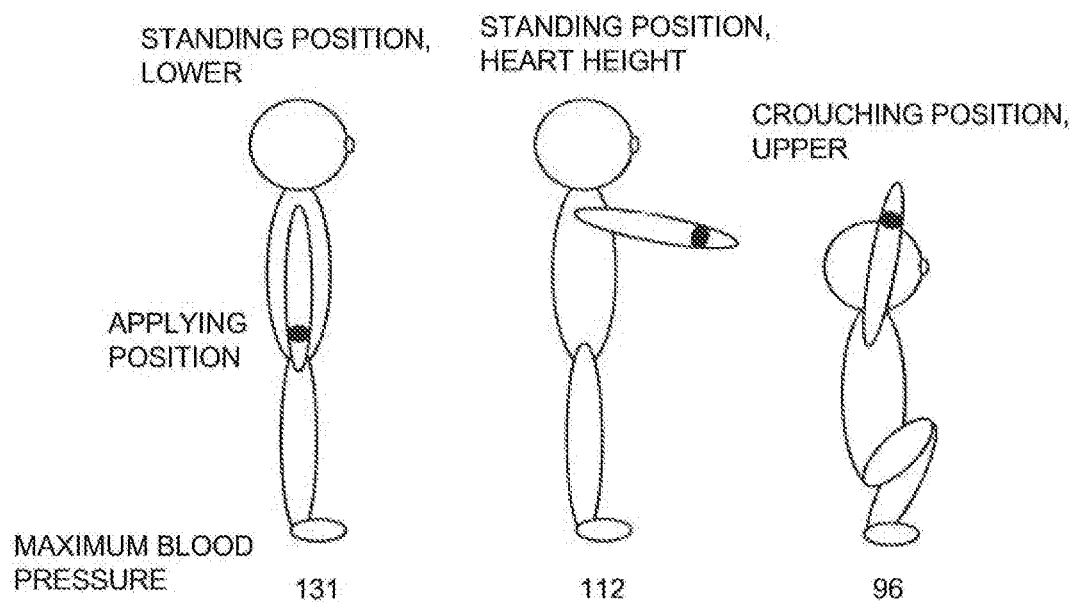
FIG. 9 shows change in blood pressure depending on the posture.

FIG. 9 shows results of measurement of change in blood pressure of a wrist depending on the posture. Even the same wrist had a difference of 131 mmHg to 96 mmHg depending on the posture. This means that the blood pressure changes largely depending on the posture, and blood pressure measurement performed at rest without body movement cannot reflect variation in actual blood pressure.

Thus, it is found that exactly measuring blood pressure in any posture is important.

Furthermore, a relationship between pulse waveforms and blood pressures will be described.

Figure 10:
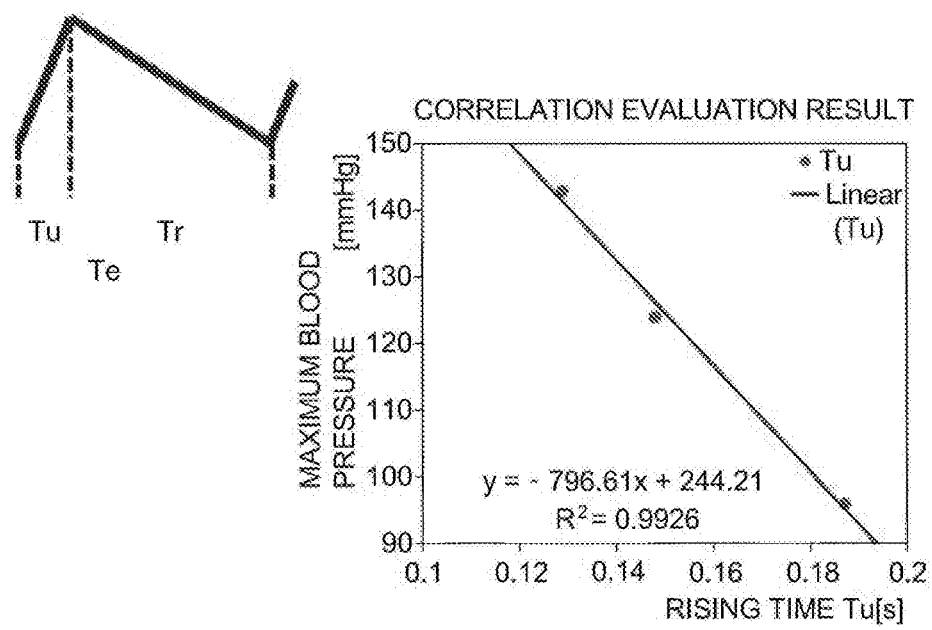
FIG. 10 shows correlation between pulse wave rising time and blood pressure value.
Figure 11:
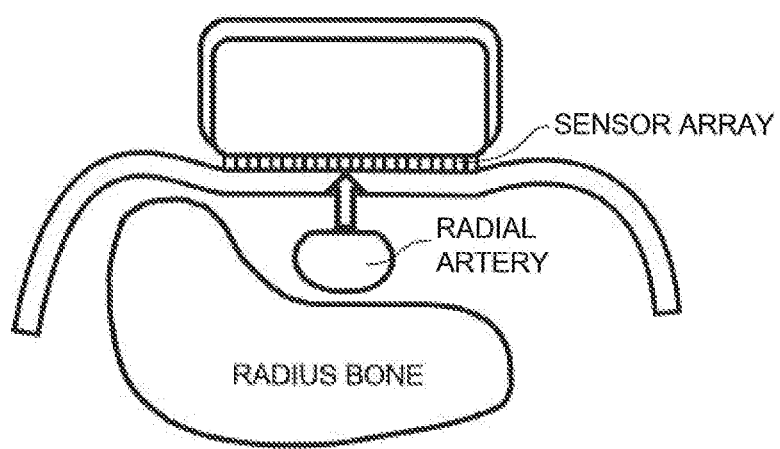
FIG. 11 shows a related art using a sensor array.

Although a correlation between the features of pulse waveforms and blood pressures is not described in detail in the present description, it has been found that there is a correlation as shown in FIG. 10 with certain accuracy in an experiment of the inventor, and it is a fact that there is generally the correlation therebetween.

The biological information calculation unit defined in the claims calculates a blood pressure value on the basis of such a pulse waveform.

Here, a shape of a pulse waveform and wave analysis thereof will be described.

In a pulse wave signal of one beat detected by the pressure sensor, a waveform rising position is referred to as "starting point", a first peak "percussion wave", a second peak "tidal wave" and a third peak "dicrotic wave". In the pulse waveform analysis, time intervals between these feature points and time intervals between feature points in adjacent pulse wave signals are each adopted as a circulatory dynamics value of a pulse wave, a parameter is extracted from the pulse waveform, and the pulse waveform analysis is performed.

Furthermore, in this pulse waveform analysis, an obtained stable pulse wave signal is differentiated first to derive a velocity pulse wave, and "starting point", "percussion wave", "tidal wave" and "dicrotic wave" information can be acquired from zero crossing points in the velocity pulse wave.

Furthermore, the velocity pulse wave is differentiated to obtain an acceleration of pulse wave, and the pulse waveform analysis can be also performed.

These obtained pulse wave signals enable blood pressure measurement, and the pulse waveform analysis contributes to determination of a human health condition, such as diagnosis of a hardness degree of a blood vessel, a cardiac disease, or the like, in addition to a blood pressure value.

The preferred exemplary embodiments of the present invention have been described above, but the present invention is not limited to these exemplary embodiments, and as a matter of course, various changes and modifications may be made without departing from the spirit and scope of the invention.

INDUSTRIAL APPLICABILITY

According to the present invention, blood pressure measurement can be performed by using an analog circuit or a digital circuit comprising a mass-producible pressure sensor and general-purpose components to effectively improve operation efficiency of, such as prediction of an unusual physical condition.

The invention claimed is:

1. A biological information reading device for reading biological information comprising:
   a biological sensor for acquiring a biological signal from a living body as an electric signal; and
   a signal processor operating as:
   a disturbance removal unit for removing a disturbance component in the electric signal acquired by the biological signal acquisition unit; and
   a biological information calculation unit for calculating a pulse waveform and a blood, pressure value as biological information on the basis of the electric signal from which disturbance is removed by the disturbance removal unit,
   wherein:
   the biological sensor includes a pulse wave detection sensor to be arranged above a blood vessel of the living body for detecting a pulse wave and an inertia detection sensor displaced from the pulse wave detection sensor,
   each of the pulse wave detection sensor and the inertia detection sensor includes a multiaxial pressure sensor, pressure detection axes thereof having different directional components respectively,
   the pulse wave detection sensor and the inertia detection sensor are configured to be attached on a skin of the living body individually so as to be not fixed in their mutual positions and to maintain the elasticity of the skin, and
   the disturbance removal unit is configured to remove inertial force components due to body movement detected by the inertia detection sensor from pulse wave components detected by the pulse wave detection sensor for respective axes.

2. The biological information reading device according to claim 1, wherein
   the biological information calculation unit includes a pulse wave circulatory dynamics calculation unit for acquiring characteristic points in a beat of a stable pulse wave signal obtained from a stable pulse wave the inertial force components due to the body movement removed from, the characteristic points including a starting point, a percussion wave, a tidal wave and a dicrotic wave, and calculating the pulse waveform and the blood pressure value by adopting at least one of mutual time intervals starting from each of the characteristic points to another, and time intervals of the characteristic points in adjacent stable pulse wave signals as a circulatory dynamics value of a pulse wave.

3. The biological information reading device according to claim 2, wherein
   the pulse wave circulatory dynamics calculation unit calculates a first differentiation of a stable pulse wave signal to derive a velocity pulse wave, and acquires the starting point, the percussion wave, the tidal wave and the dicrotic wave from zero crossing points in the velocity pulse wave.

4. The biological information reading device according to claim 1, wherein
   the multiaxial pressure sensor includes a MEMS sensor.

5. The biological information reading device according to claim 1, wherein
   the multiaxial pressure sensor includes a capacitive sensor.

* * * * *